(12) United States Patent
Fauza

(10) Patent No.: US 6,612,305 B2
(45) Date of Patent: Sep. 2, 2003

(54) INTEGRAL BALLOON TRACHEOSTOMY TUBE

(76) Inventor: Dario O. Fauza, 17 Ledyard St., Wellesley, MA (US) 02481-1607

( * ) Notice: Subject to any disclaimer, the term of this patent is extended or adjusted under 35 U.S.C. 154(b) by 0 days.

(21) Appl. No.: 09/844,044

(22) Filed: Apr. 27, 2001

(65) Prior Publication Data

US 2002/0007833 A1 Jan. 24, 2002

Related U.S. Application Data

(60) Provisional application No. 60/201,449, filed on May 3, 2000.

(51) Int. Cl.$^7$ ............................................. A61M 16/00
(52) U.S. Cl. ............................ 128/200.26; 128/207.15; 128/207.29
(58) Field of Search ...................... 128/200.26, 207.15, 128/207.29

(56) References Cited

U.S. PATENT DOCUMENTS

| | | | | |
|---|---|---|---|---|
| 2,693,182 A | * | 11/1954 | Phillips ................. | 128/200.26 |
| 3,543,751 A | | 12/1970 | Sheffer | |
| 3,688,774 A | * | 9/1972 | Akiyama ............... | 128/200.26 |
| 3,889,688 A | | 6/1975 | Eamkaow | |
| 3,973,569 A | * | 8/1976 | Sheridan et al. ....... | 128/207.15 |
| 3,987,798 A | * | 10/1976 | McGinnis .............. | 128/207.15 |
| 4,033,353 A | | 7/1977 | La Rosa | |
| 4,305,392 A | * | 12/1981 | Chester ................. | 128/207.15 |
| 4,327,721 A | * | 5/1982 | Goldin et al. .......... | 128/207.15 |
| 4,449,523 A | * | 5/1984 | Szachowicz et al. ... | 128/200.26 |
| 4,573,460 A | * | 3/1986 | Szachowicz et al. ... | 128/200.26 |
| 4,598,705 A | * | 7/1986 | Lichtenberger ........ | 128/200.26 |
| 4,791,920 A | | 12/1988 | Fauza | |
| 5,056,515 A | | 10/1991 | Abel | |
| 5,515,844 A | * | 5/1996 | Christopher ........... | 128/207.29 |
| 5,983,895 A | | 11/1999 | Turner | |

FOREIGN PATENT DOCUMENTS

EP 0 106 780 A 4/1984

* cited by examiner

*Primary Examiner*—Aaron J. Lewis
(74) *Attorney, Agent, or Firm*—Holland & Knight LLP

(57) ABSTRACT

The present invention relates to a tracheostomy device with an inflatable balloon (1) attached to a hollow tube (2) by means of two areas of adhesion (1a and 1b) whose ortogonal projections are not contiguous or, in other words, are at an angle (α) other than 180°. This balloon (1) communicates with the environment by means of a capped, valved flexible conduit (4). A movable flange (3) allows for extra fixation of the device around a patient's neck. A displaceable inner tube (5) can be removed in case of severe acute obstruction, allowing for immediate establishment of air flow. The design and distribution of the components of this tracheostomy device contribute to increased safety and comfort of tracheostomies by: enhancing the its anchorability, hence better stabilizing it within the trachea; improving its placement within the airway; increasing the volume, hence lowering the pressure inside its balloon (1); enhancing the balloon's (1) volume-to-pressure curve; completely sealing the trachea from the tracheostomy wound, larynx and pharynx; shortening the tube (2) size and providing a movable neck flange (3).

6 Claims, 2 Drawing Sheets

INTEGRAL BALLOON TRACHEOSTOMY TUBE

This application claims the benefit of Provisional Application No. 60/201,449 filed May 3, 2000.

FIELD OF THE INVENTION

The present invention generally relates to a surgical device used in a tracheostomy, which is a surgically produced airway introduced directly through the trachea, below the vocal cords.

BACKGROUND OF THE INVENTION

The vast majority of tracheostomy tubes in current use follow a basic concept consisting of a curved tube which serves as an artificial passage for exchange of air between a patient and an air source, typically either atmospheric air or a mechanical respirator. See, for example U.S. Pat. No. 5,983,895 to Turner. The tube often is enveloped at its caudal end by a small, inflatable balloon, also called a cuff, which is fillable with a fluid, such as air, as it is often necessary to employ positive inspiratory pressure by means of a respirator. See for example, U.S. Pat. No. 5,056,515 to Abel and U.S. Pat. No. 4,791,920 to Fauza. The balloon adheres to the internal lining of the trachea in its cross-section in order to prevent air insufflated by a respirator into a patient from escaping to the environment through the tracheostomy or the larynx and pharynx, which enables the air to reach the lower airways and eventually the pulmonary alveoli. The balloon also aids in supporting the tube inside the trachea.

These conventional tube designs, however, contribute to a variety of frequent complications associated with tracheostomies. Most of these complications are consequences of both the instability of the tube inside the trachea and the pressure inside the balloon.

Instability of the Trachea Tube

Trachea tubes are one of the few, if not only, ballooned tubes currently used in different areas of the human body that are not truly anchored within the body. Consequently, the tube moves a great deal inside the airway, as well as through the tracheal stoma and the wound. This problem is universally observed. Tracheostomy tubes frequently are misplaced inside the trachea, because of this instability and lack of anchorage, leading to a number of different ventilatory problems. Tracheostomy tubes also can be accidentally dislocated, sometimes coming off the airway completely, with possible impaired ventilation, brain damage, or even death in some cases, as reintroduction of the tube can be very difficult.

The continual movement of tracheostomy tubes, for example, due to the rhythm of an artificial ventilator and movements by the patient, is responsible for direct damage to the trachea, mainly at the cranial level of the stoma. One of the most common complications of tracheostomy is stenosis (or stricture) of the trachea at the level of the stoma, which is primarily caused by continual movement of the tube against that area of the trachea, directly damaging the cartilaginous rings. According to studies, a significant proportion of the patients that undergo tracheostomy will have some degree of stenosis of the trachea, usually at the cranial level of the stoma, where the curved portion of the tube produces even more injury as a consequence of its continual movement. This stenosis in turn may produce several long term clinical manifestations, such as intolerance to exercise and recurrent infections, which may require in some patients removal of part of the trachea.

The instability of the tube can also be responsible for other more dramatic complications, for example, damage to the trachea distal (or caudal) to the stoma which results in total perforation of the trachea or structures adjacent the trachea, including the esophagus or the innominate artery. If the innominate artery is perforated, there is a so-called tracheo-innominate artery fistula, with mortality rates around 95%. This kind of fistula may also result from an inflammatory reaction around the stoma that is more intense if there is repeated injury to the area from continual movement of the tube. Those more dramatic, life-threatening complications are rare, but still a possibility nowadays.

Balloon Pressure

High pressures inside the balloon have long been identified as a major cause of damage to the tracheal wall. Such damage may also result in stenosis and/or perforation of the trachea. The concept of a high-volume-low-pressure balloon was introduced in the 1970s, with great impact on the market, exactly because it significantly reduced the pressures inside the balloon and, consequently, the rate and severity of many complications, as compared to previous low-volume-high-pressure balloons. This balloon concept has been used as the "standard" for approximately 30 years. The high-volume-low-pressure balloon, however, is still linked to complications, primarily for two reasons: (1) after a certain degree of expansion, the volume-to-pressure curve of the balloon changes towards that of a low-volume-high-pressure balloon because there is little additional volume inside the balloon, depending on how tight the tube fits inside the trachea; and (2) the continual movement of the tube makes the volume (and thus the pressure) in the balloon very unstable, and also directly forces the balloon against the tracheal wall. Consequently, stenosis and perforation of the trachea still occur at or near the location of the balloon.

It would therefore be desirable to provide a tracheostomy tube and balloon design that is more stable within the patient than currently available tubes, while minimizing pressures within the balloons, thus reducing the occurrence of stenosis and perforations.

Other Design Deficiencies

Infection remains a primary complication of tracheostomy. According to recent reports, approximately 66% of patients with tracheostomies have nosocomial pneumonia and 100% of them have colonization of the airways with bacteria and/or fungi. These complications are primarily due to direct communication between the trachea and the wound through the stoma (and consequently between the trachea and the environment) and aspiration of contents of the pharynx. It would be advantageous to develop a tracheostomy tube and balloon design that is minimizes or prevents infection resulting from these sources.

Another relatively frequent and potentially major complication is obstruction of the tracheostomy tube by mucous plugs. Constant toilette of the tube is mandatory. Another, comparatively minor, complication is the discomfort and/or skin damage caused by straps around the neck that are required to prevent displacement of the tracheostomy tube.

It is therefore an object of this invention to a tracheostomy tube and balloon assembly that is stable within the patient and which minimizes pressures within the balloon in order to avoid or minimize complications associated with the use of standard tracheostomy tube designs.

SUMMARY OF THE INVENTION

The present invention relates to a tracheostomy tube with the format and distribution of its balloon designed so as to increased safety of tracheostomies by: enhancing the tube's anchorability, hence better stabilizing it within the trachea; improving tube placement within the airway; increasing volume, hence lowering the pressure inside the balloon; enhancing the balloon's volume-to-pressure curve; completely sealing the trachea from the tracheostomy wound, larynx and pharynx; shortening the tube size and providing a movable neck flange.

DETAILED DESCRIPTION OF THE INVENTION

Figure 1:
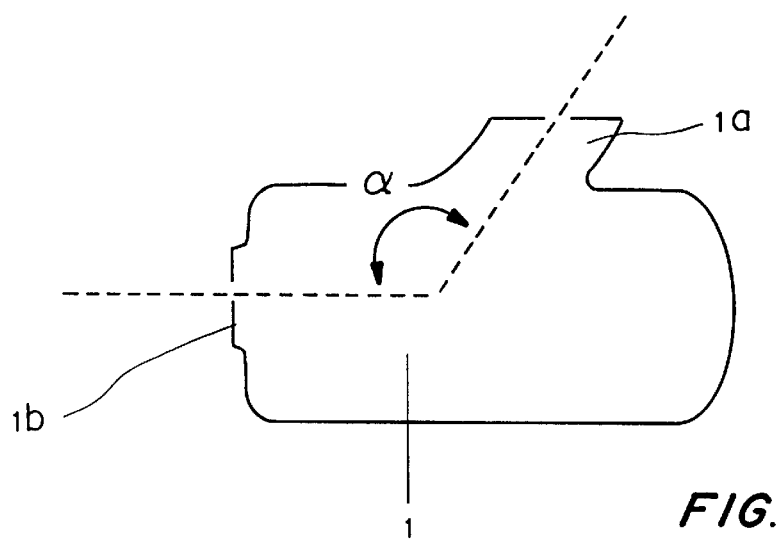
FIG. 1 is a side elevational view of a preferred embodiment of the tracheostomy tube.
Figure 2:
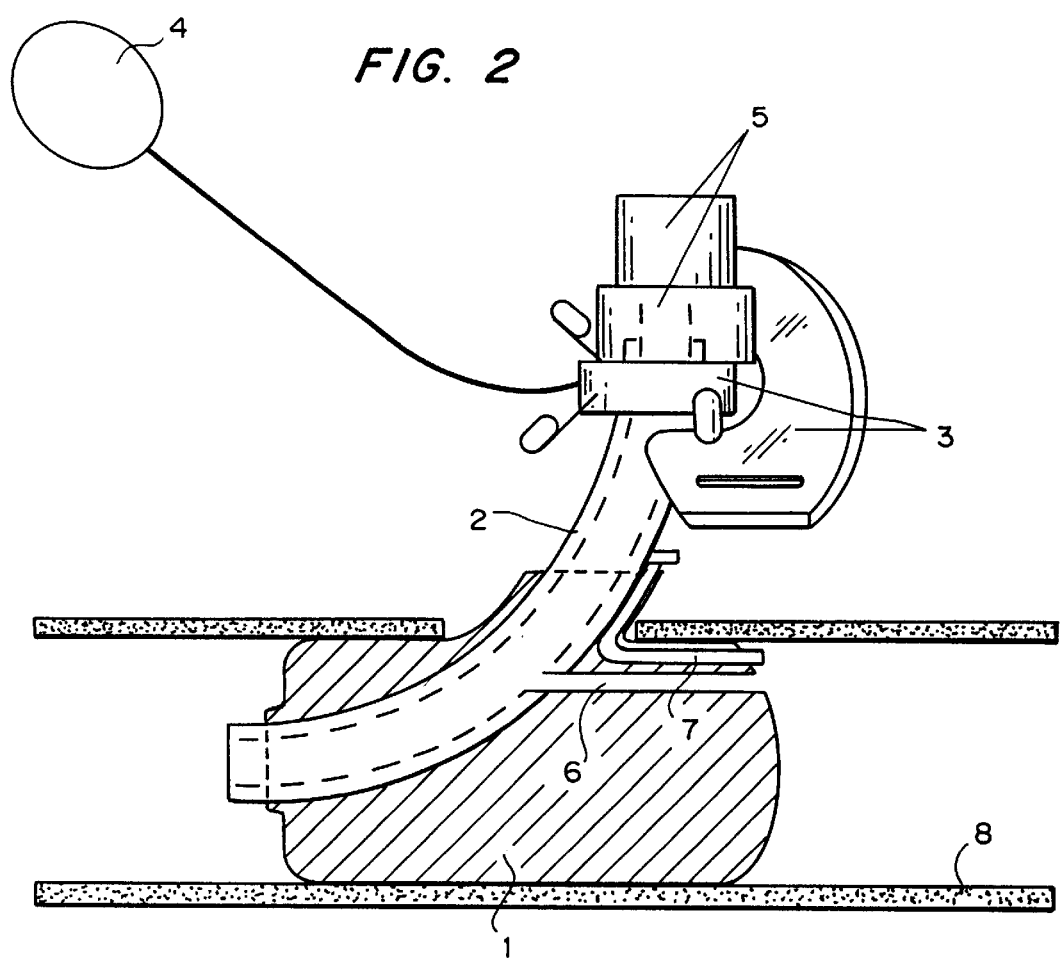
FIG. 2 is a perspective view of the tracheostomy tube of FIG. 1.
Figure 3:
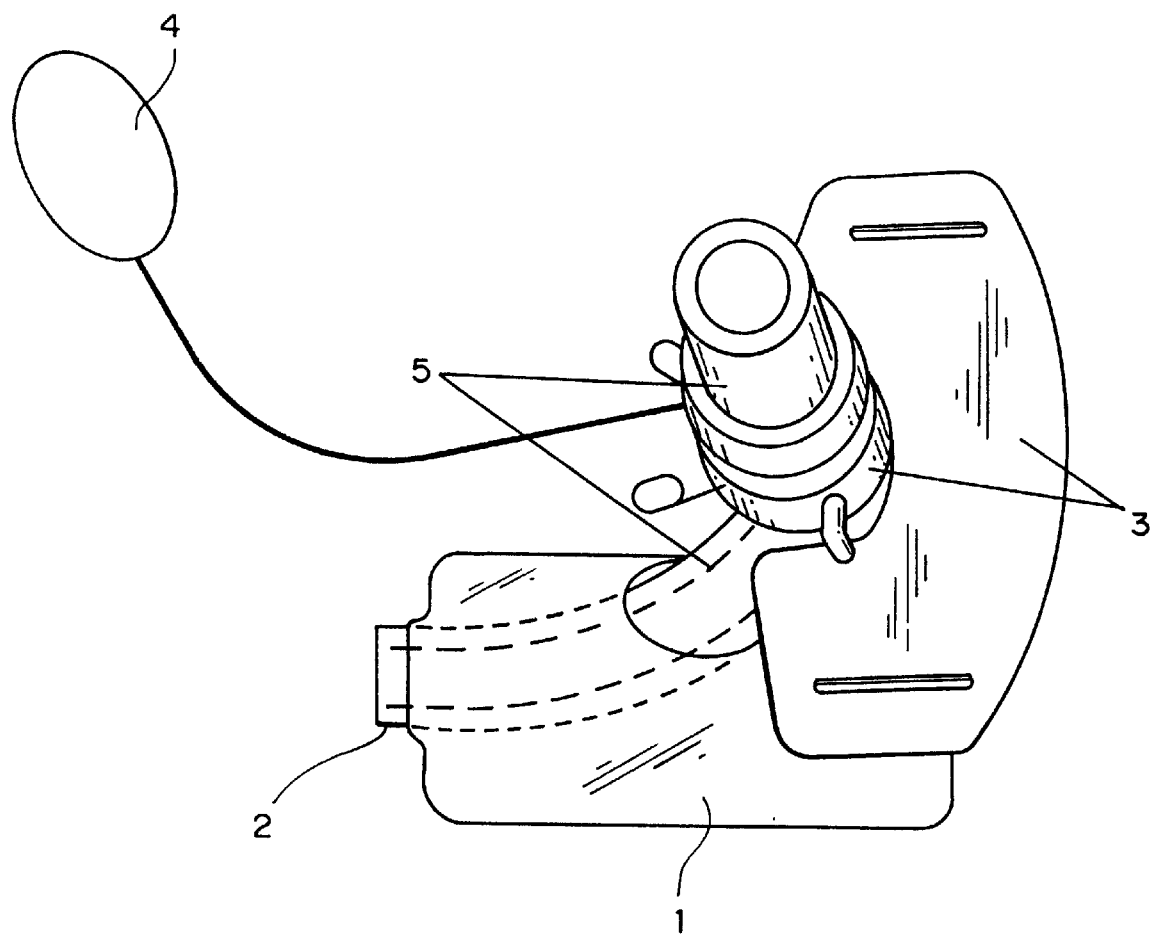
FIG. 3 is a side elevational view of the inflatable balloon component of the tracheostomy tube of FIG. 1.

The tracheostomy tube of the present invention can be better understood with reference to FIGS. 1–3, which are described below.

The main difference of the present invention, when compared with the current state of the art, is its balloon (1). It has an "integral" design, expanding not only around the tube (2), as do the current models, but also cranially to it and to the stoma. This is achieved by the fact that the orthogonal projections of the two areas of attachment between this balloon (1) and the tube (2), namely (1a) and (1b), are not contiguous or, in other words, are at an angle (α) other than 180°, as it is the case in current models. The six most important consequences of that are: a) this balloon (1) design anchors the tube (2) inside the trachea (8) because it expands both distally and cranially to the stoma, stabilizing the tube (2) completely and consequently dramatically minimizing, if not completely avoiding, movement or "play" of the tube (2) through the trachea, the stoma and the wound; b) this balloon (1) design, by definition, also ensures that the tip of the tube (2) is always properly placed inside the trachea (8) and never pointing in any direction other than the distal airways and lungs; c) the cranial expansion of this balloon (1) greatly enlarges its volume and consequently significantly lowers the pressure inside it; d) the cranial expansion of this balloon (1) acts as a sort of "escape valve", making its volume-to-pressure curve much better than that of the current ones, that is, even with the injection of large volumes of air inside the balloon (1), there is very little increase of the pressure inside it; e) this balloon (1) completely seals the tracheal stoma, impeding direct communication between the trachea and the wound or the environment, thus minimizing the risk of contamination or infection; and f) the better tracheal sealing produced by this balloon (1) minimizes the chances of aspiration from the pharynx.

The tube (2) itself is practically the same as that found in current models. The only difference is that, because of the above-mentioned characteristics of the balloon (1), it is shorter, which in turn: a) minimizes even more the possibility of "play" or movement of the tube (2); b) lowers, if not totally eradicates, the risk of tracheo-innominate artery fistula (because it doesn't reach the area of intersection of the trachea with that artery); c) diminishes the resistance to air flow; and d) provides for an easier toilette of the tube (2) through suction catheters. This tube can have double lumen, in other words an internal movable inner tube (5), which can be removed in case of severe acute obstruction of it, for example by mucous secretions, allowing for immediate establishment of air flow through the outer tube (2) and for easier cleaning of the inner tube (5).

Insufflation of the balloon (1) is by means of a capped, valved flexible conduit (4) that connects the balloon (1) to the environment. A movable neck flange (3) adds to safety by allowing strap fixation around the patient's neck at different distances from the balloon (1), depending on the local anatomy. The possibility to move this flange (3) is helpful, given the absolute anchorability of the tube (2).

The resulting stability of this tube (2), the very low pressure inside its balloon (1), its balloon's (1) volume-to-pressure curve and the shorter length of its tube (2) should all help to significantly minimize, if not completely eradicate, most, if not all, relevant complications of tracheostomy that are dependent on both the lack of anchorage of the current models and on the pressure profile of their balloons. Yet another advantage is that, because of its balloon's (1) "integral" design, the trachea should stay totally sealed, isolated from the wound and the environment, at the same time that it is much more difficult for the patient to aspirate contents from the pharynx. As a consequence of all that, the rate and severity of infections should be much lower than those observed with the current models. Moreover, because this tube (2) is so stable, the patient doesn't necessarily have to wear the sometimes uncomfortable straps around the neck.

The functions of the tracheostomy tube of present invention are the same as those achieved by current models, only at much higher levels of safety and comfort. No change is necessary in the well-established surgical technique of tracheostomy itself for the device of the present invention to be employed.

The tracheostomy cannula of the invention may, starting from the basic concept described above, undergo some changes such as in its dimensions, which vary according to the patient's anatomical characteristics, as ell as in its design, which may present the following variations. The posterior, or cranial, aspect of the tube (2) and inner tube (5) may, or not, have an orifice (6) that would permit the passage of air from the lungs to the vocal cords, thus allowing the patient to speak. For that variation of the basic design to be functional, however, yet another orifice would need to be present on the posterior or cranial aspect of the balloon (1) and such orifice (6) would need to be sealable and in communication with the said orifice on the tube. Another possible design variation is the presence of an extra capped, valved flexible conduit (7) along the tube (2) and the balloon (1), that connects the posterior, or cranial, aspect of the balloon (1) inside the trachea to the environment, so that secretions eventually accumulating cranially to the tracheal stoma could be removed.

Modifications and variations of the present invention will be obvious to those of skill in the art from the foregoing detailed description. Such modifications and variations are intended to come within the scope of the following claims.

I claim:

1. A tracheostomy tube device comprising:
   a hollow tube having a proximal end portion, a distal end portion, and a bend intermediate of the end portions, wherein the distal end portion is arranged for insertion through a patient's throat and tracheal stoma and into the tracheal lumen such that the distal end portion of the tube extends in a first direction within the tracheal lumen when the proximal end portion extends in a second direction through the tracheal stoma;

an inflatable balloon including orthogonal projections that are discontiguous with respect to each other, attached to the hollow tube both at the proximal end portion and at the distal end portion at the respective orthogonal projections, providing for expansion of the balloon around both the proximal end portion and the distal end portions of the tube;

means for inflating and deflating the balloon; and flange means connected to the proximal end portion of the tube, suitable for securing the distal end portion of the tube within the tracheal lumen, wherein the flange means provides an anchoring point external the patient's throat.

2. The tracheostomy tube device of claim 1 wherein the balloon can be inflated to completely seal the trachea (i) cranially and caudally to the tracheal stoma, and (ii) at the level of the tracheal stoma.

3. The tracheostomy tube device of claim 1 wherein the flange means is movable along at least a portion of the tube, so as to accommodate to different anatomic characteristics of the patient's neck.

4. The tracheostomy tube device of claim 1 wherein the means for inflating and deflating the balloon comprises a flexible conduit in communication with the balloon.

5. The tracheostomy tube device of claim 1 wherein the tube comprises a first orifice and the balloon comprises a second orifice sealable and in communication with the first orifice, through both of which air can flow to allow the patient to speak.

6. The tracheostomy tube device of claim 1 further comprising a flexible conduit along both the tube and the balloon connects the posterior, or cranial, aspect of the balloon, within the first direction inside the trachea, to the environment, such that secretions eventually accumulating cranially to the tracheal stoma can be removed.

* * * * *